United States Patent
Gigler

(10) Patent No.: US 9,782,752 B2
(45) Date of Patent: Oct. 10, 2017

(54) METHOD FOR PROVIDING AN ACTIVE RUTHENIUM CATALYST SOLUTION FOR THE TRANSVINYLATION OF CARBOXYLIC ACIDS

(71) Applicant: Wacker Chemie AG, Munich (DE)

(72) Inventor: Peter Gigler, Dachau (DE)

(73) Assignee: Wacker Chemie AG, Munich (DE)

(*) Notice: Subject to any disclaimer, the term of this patent is extended or adjusted under 35 U.S.C. 154(b) by 0 days.

(21) Appl. No.: 15/127,619

(22) PCT Filed: Mar. 23, 2015

(86) PCT No.: PCT/EP2015/056099
§ 371 (c)(1),
(2) Date: Sep. 20, 2016

(87) PCT Pub. No.: WO2015/154978
PCT Pub. Date: Oct. 15, 2015

(65) Prior Publication Data
US 2017/0152208 A1    Jun. 1, 2017

(30) Foreign Application Priority Data
Apr. 10, 2014  (DE) .................. 10 2014 206 915

(51) Int. Cl.
| B01J 23/46 | (2006.01) |
| C07C 67/343 | (2006.01) |
| B01J 35/12 | (2006.01) |
| B01J 37/16 | (2006.01) |

(52) U.S. Cl.
CPC ............ B01J 23/462 (2013.01); B01J 35/12 (2013.01); B01J 37/16 (2013.01); C07C 67/343 (2013.01)

(58) Field of Classification Search
None
See application file for complete search history.

(56) References Cited

U.S. PATENT DOCUMENTS

| 4,981,973 | A | 1/1991 | Murray |
| 5,155,253 | A | 10/1992 | Murray |
| 5,210,207 | A | 5/1993 | Mokhtarzadeh et al. |
| 2014/0343310 | A1 | 11/2014 | Johnen et al. |
| 2014/0357881 | A1 | 12/2014 | Johnen et al. |

FOREIGN PATENT DOCUMENTS

| DE | 102013224491 A1 | 6/2015 |
| DE | 102013224496 A1 | 6/2015 |
| EP | 0351603 A2 | 1/1990 |
| EP | 0497340 A2 | 8/1992 |
| EP | 0506070 A2 | 9/1992 |
| EP | 0376075 B1 | 6/1994 |
| WO | 9209554 A1 | 6/1992 |
| WO | 2013117294 A1 | 8/2013 |
| WO | 2013117295 A1 | 8/2013 |
| WO | 2015078746 A1 | 6/2015 |
| WO | 2015078747 A1 | 6/2015 |

OTHER PUBLICATIONS

Ziriakus. "Ruthenium-catalyzed transvinylation". Dissertation, Technical University of Munich, pp. 1-160 (2012).
Ziriakus et al., "Ruthenium-Catalyzed Transvinylation—New Insights". Adv. Synth. Catal., 355: pp. 2845-2859 (2013).
International Search Report for PCT/EP2015/056099 dated Jun. 15, 2015.

*Primary Examiner* — Yate K Cutliff
(74) *Attorney, Agent, or Firm* — Caesar Rivise, PC

(57) ABSTRACT

The invention relates to a method for providing a ruthenium catalyst solution which is active during the transvinylation of a surfactant vinyl ester with a surfactant carboxylic acid, comprising an Ru metal concentration of more than 0.5 wt. % based on the total weight of the ruthenium catalyst solution. The invention is characterized in that a) at least one ruthenium (III) halogenide with at least one inorganic or organic base, at least one surfactant vinyl ester, and at least one surfactant carboxylic acid is reacted at a temperature of 70° C. to 170° C.; b) the molar ratio of surfactant vinyl ester to surfactant carboxylic acid is 1:1.8 to 1.8:1; and c) the ruthenium (III) halogenide is used in a quantity of >0.5 wt. % of Ru metal based on the total weight of the surfactant vinyl ester and surfactant carboxylic acid.

10 Claims, No Drawings

METHOD FOR PROVIDING AN ACTIVE RUTHENIUM CATALYST SOLUTION FOR THE TRANSVINYLATION OF CARBOXYLIC ACIDS

BACKGROUND OF THE INVENTION

The invention relates to a method for the preparation an active Ru catalyst solution for the transvinylation of carboxylic acids and use thereof in the transvinylation of carboxylic acids.

The transvinylation of carboxylic acids serves to produce vinyl esters. This is understood to mean the transfer of a vinyl unit of a reactant vinyl ester (1V) to a reactant carboxylic acid (2S) to generate a product vinyl ester (2V) and the corresponding acid of the reactant vinyl ester (1S).

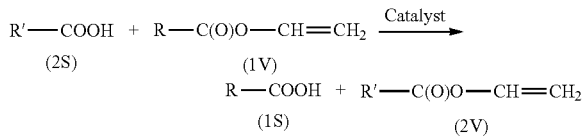

The transvinylation of vinyl esters with carboxylic acids in the presence of palladium catalyst is known from EP 376075 B1, in which copper bromide and especially lithium compounds are used as cocatalysts.

In addition to palladium catalysts and mercury catalysts, ruthenium compounds are also used as catalyst in the prior art for transvinylation of vinyl esters with carboxylic acids. Ruthenium compounds are characterized by their high solubility, low volatility and high thermal stability. In addition, they have high, temperature-inducible activity.

A method for transvinylation of carboxylic acids using various Ru compounds as catalyst precursor is described in EP 351603 A2 (=EP506070, U.S. Pat. No. 4,981,973, U.S. Pat. No. 5,155,253). The authors postulate a [Ru(CO)$_2$RCO$_2$] unit as a critical structural element in the formation of the active species. Consequently, all Ru compounds may be used as catalyst precursors which can be converted in situ into this structural element. When using ruthenium(III) chloride as starting compound, the addition of an alkali metal carboxylate is required to generate the active species. Example 16 describes the transvinylation of benzoic acid (100 mmol) with vinyl acetate (200 mmol) using a RuCl$_3$/sodium acetate mixture, which is converted in situ under the transvinylation conditions to the active catalyst compound. After a reaction time of one hour in the transvinylation at 130° C., a yield of 27% of vinyl benzoate is achieved.

In Adv. Synth. Catal. 2013, 355, 2845-2859 the theory of EP 351603 A2 is confirmed and a [Ru(CO)$_3$(RCO$_2$)$_2$] complex as active catalyst species is postulated. The formation of the catalytically active species takes place by the reaction of RuCl$_3$ with sodium hydroxide, vinyl acetate (reactant vinyl ester) and propionic acid (reactant carboxylic acid). The reaction takes place over 4 hours at a temperature of 140° C. and a molar ratio of vinyl acetate to propionic acid of 2.7:1. The yield of active ruthenium catalyst is stated as 53%.

EP 497340 A2 (U.S. Pat. No. 5,210,207) describes a transvinylation process for preparing product vinyl esters whose boiling points are higher than those of the reactant vinyl esters. By reactive distillation of at least one of the product components, the reaction equilibrium is shifted to the product side. The Ru catalysts described in EP 351603 A2 are preferably used for this purpose. Examples in which the active catalyst species are generated from RuCl$_3$ and are used are not stated. The active Ru catalysts used are Ru carbonyl acetate and Ru dicarbonyl acetate.

A method is described in WO 92/09554 A1 in which the reaction mass is firstly separated after the transvinylation and the product vinyl ester is subsequently separated by azeotropic distillation. This method focuses especially on the separation of acid/vinyl ester mixtures with low boiling point differences. The Ru catalysts from EP 351603 A2 (Ru carbonyl acetate and Ru dicarbonyl acetate) are preferably used in the transvinylation reaction. The use of RuCl$_3$-based catalyst systems is not described in the examples.

WO 2013/117294 A1 describes a continuous method for preparing carboxylic vinyl esters. The transition metal catalysed transvinylation is operated in the steady-state and the reaction mixture is separated in a subsequent step. WO 2013/117295 describes a further configuration of this process with a subsequent derivatization of the resulting conjugate acid of the reactant vinyl ester. In the examples of both documents, Pd catalysts are mainly used for the transvinylation. RuCl$_3$-based catalysts are not described.

The use of Ru catalysts in the transvinylation reaction has distinct advantages compared to Pd catalysts with respect to solubility, volatility, thermal stability and thermally inducible activity. Numerous Ru compounds can be converted in situ to active Ru species which catalyse the transvinylation reaction. The specific preparation of a concentrated active catalyst solution based on industrially available ruthenium halides is not known.

Therefore, the object consisted of developing a method for preparing an active Ru catalyst solution having an Ru concentration of more than 0.5%, which is characterized by a high Ru yield based on the ruthenium halide used and a high activity.

DESCRIPTION OF THE INVENTION

The invention relates to a method for the preparation of an active ruthenium catalyst solution, in the transvinylation of a reactant vinyl ester with a reactant carboxylic acid, having a ruthenium concentration greater than 0.5% by weight of Ru metal, based on the total weight of the ruthenium catalyst solution, characterized in that a) at least one ruthenium(III) halide is reacted with at least one inorganic or organic base, at least one reactant vinyl ester and at least one reactant carboxylic acid, at a temperature of 70° C. to 170° C., wherein b) the molar ratio of reactant vinyl ester to reactant carboxylic acid is from 1:1.8 to 1.8:1, and c) the ruthenium(III) halide is used in an amount of ≥0.5% by weight of Ru metal based on the total weight of reactant vinyl ester and reactant carboxylic acid.

An active ruthenium catalyst solution is here understood to mean a solution of one or more ruthenium compounds which catalyzes the transvinylation of a reactant vinyl ester with a reactant carboxylic acid without an additional formation step.

The ruthenium(III) halides used may be ruthenium(III) chloride, ruthenium(III) bromide and Ru(III) iodide. Preference is given to using ruthenium(III) chloride. The Ru(III) halide is typically used at concentrations of ≥0.5% by weight (ruthenium content based on the reaction mass of reactant vinyl ester and reactant carboxylic acid). The upper limit is preferably 4% by weight (ruthenium content based on the reaction mass of reactant vinyl ester and reactant carboxylic acid). Particularly preferred are concentrations of 0.75% by weight to 3% by weight and most preferred are concentrations of 1% by weight to 2% by weight, ruthenium content being based in each case on the reaction mass of reactant vinyl ester and reactant carboxylic acid.

The bases used may be inorganic bases such as hydroxides, carbonates and hydrogen carbonates of the alkali metals and alkaline earth metals, ammonia and also organic bases such as carboxylates and alkoxides of the alkali metals and alkaline earth metals and organic amines. Preference is given to using hydroxides and carboxylates of the alkali metals and alkaline earth metals. Examples of these are NaOH, KOH, Na acetate, K acetate. Particular preference is given to using sodium hydroxide. In general, 1 to 10 mole equivalents of base per mole of ruthenium(III) halide are used in each case. Preference is given to using 2 to 5 mole equivalents, particular preference being given to 3 mole equivalents.

The vinyl ester used can be any carboxylic vinyl ester of the general formula R—C(O)O—CH=CH$_2$, where R may be an aliphatic residue having 1 to 12 carbon atoms, or may be a cycloaliphatic residue having up to 12 carbon atoms, or may be an aromatic residue having up to 12 carbon atoms. Preference is given to the use of low molecular weight reactant vinyl esters, where R is an alkyl residue having 1 to 6 carbon atoms, for example vinyl acetate, vinyl propionate and vinyl pivalate. Particular preference is given to using vinyl acetate.

Furthermore, at least one reactant carboxylic acid of the general formula R'—COOH is added to the reaction, where R' may be an aliphatic residue having 1 to 22 carbon atoms, or may be a cycloaliphatic residue having up to 22 carbon atoms, or may be an aromatic residue having up to 22 carbon atoms. Preference is given to using reactant carboxylic acids of the compound classes stated having 2 to 18 carbon atoms. Examples of these are acetic acid, propionic acid, n-butyric acid, isobutyric acid, n-valeric acid, 2-methylbutyric acid, 3-methylbutyric acid, pivalic acid, caproic acid, cyclohexanecarboxylic acid, n-heptanoic acid, 2-methylhexanoic acid, 2-ethylhexanoic acid, n-octanoic acid, n-nonanoic acid, isononanoic acid, neononanoic acid, n-decanoic acid, neodecanoic acid, lauric acid, myristic acid, palmitic acid, stearic acid, benzoic acid, naphthalenecarboxylic acid. Particular preference is given to versatic acids[R] (alpha-branched carboxylic acids having 9 to 12 carbon atoms from Momentive) or neo acids having 9 to 12 carbon atoms and fatty acids such as lauric acid, myristic acid, palmitic acid and stearic acid.

The molar ratio of reactant vinyl ester to reactant carboxylic acid may be from 1:1.8 to 1.8:1. Preference is given to a ratio of reactant vinyl ester to reactant carboxylic acid of from 1.5:1 to 1:1, particular preference being given to a ratio of circa 1:1.

Optionally, a polymerization inhibitor can be added to the reactants specified. Preference is given to using 100 to 10 000 ppm polymerization inhibitor, based on the reaction mass of reactant vinyl ester and reactant carboxylic acid. Examples of polymerization inhibitors are hydroquinone, methoxyhydroquinone, tertiary-butyl catechol, phenothiazine or nitroxide radicals such as TEMPO or 4-OH-TEMPO (TEMPO=2,2,6,6-tetramethylpiperidinyloxyl). Preference is given to the use of phenothiazine or hydroquinone.

The reactants may be supplied individually or as a mixture, and are reacted in one or more steps at a temperature of 70° C. to 170° C.

In a preferred embodiment, base, reactant carboxylic acid and optionally polymerization inhibitor are pretreated in the reactor at a temperature of preferably 80° C. to 160° C., particularly preferably 120° C. to 140° C., and a pressure of preferably less than or equal to 1 bar abs. for preferably 0.5 h to 3 h, particularly preferably 1 h. Resulting water of reaction can optionally be evaporated off or be removed under reduced pressure. Subsequently, the Ru(III) halide may be added and the reaction continued, preferably under the same pressure and temperature conditions, for preferably a further 0.25 h to 2 h, particularly preferably 0.5 h to 1 h. The reactant vinyl ester is then preferably added and, at a temperature of 70° C. to 170° C., preferably at a temperature of 120° C. to 150° C., the pressure is generally increased to >1 bar abs., and the reaction is continued under these conditions for 8 h to 16 h. The reaction is preferably carried out in a protective gas atmosphere, nitrogen for example, in a manner known per se. The reaction time in the method according to the invention is generally in total 1 to 24 hours, preferably 8 to 20 hours, particularly preferably 12 to 17 hours.

After the reaction, undissolved constituents can be removed by filtration, extraction, sedimentation or precipitation. Undissolved constituents are preferably removed by filtration.

Optionally, the Ru catalyst solution thus obtained may be further concentrated by distillation.

The substeps of the method, both the reaction and the work-up steps, may be carried out batchwise, semi-continuously and in non-stop mode. The method is preferably carried out in batch mode.

Using the method according to the invention, active Ru catalyst solutions may be prepared at a concentration of ruthenium, in catalytically active and soluble form, of greater than 0.5% by weight, based on the total weight of the solution. It has been found, surprisingly, that at a vinyl ester to carboxylic acid ratio in the range claimed of from 1:1.8 to 1.8:1, more than 80% by weight of the ruthenium used can be converted into a soluble and active form.

The method according to the invention therefore enables the preparation of an active, highly concentrated catalyst solution (greater than 0.5% by weight ruthenium content based on a mixture (solvent) largely composed of product vinyl ester, the conjugate acid of the reactant vinyl ester, reactant vinyl ester and reactant carboxylic acid), based on commercially available ruthenium halides. The initiation phase, which occurs when using catalyst precursors, can be avoided by using preformed catalyst solutions of this kind.

The invention also relates to the use of the Ru catalyst solution according to the invention in the transvinylation of a reactant carboxylic acid with a reactant vinyl ester to give a product vinyl ester and the corresponding acid of the reactant vinyl ester. Such methods for the transvinylation of carboxylic acids by means of ruthenium catalysis are known to those skilled in the art, for example from the published specifications DE 102013224491 and DE 102013224496.

EXAMPLES

The following examples serve to illustrate the invention in more detail.

The Ru yield is calculated according to A (%)=100×m$_{Ru}$(F)/(m$_{Ru}$(F)+m$_{Ru}$(FK)), where m$_{Ru}$(F) represents the mass of ruthenium in the filtrate and m$_{Ru}$(FK) represents the mass of ruthenium in the filter cake.

Comparative Example 1

Preparation of a Catalyst Solution with Low Ru Concentration (<0.5% by Weight) and a Vinyl Ester/Acid Ratio of 2:1

Into a 100 ml Berghoff autoclave were introduced 38.5 g (0.19 mol) of lauric acid, 0.26 g (6.5 mmol) of sodium hydroxide, 0.07 g of phenothiazine and the mixture was heated to 120° C. for 1 hour such that resulting water of reaction could escape. Subsequently, 0.60 g (2 mmol) of ruthenium(III) chloride hydrate was added and the mixture heated to 120° C. for a further half an hour such that water could escape. After addition of 33.0 g (0.38 mol) of vinyl acetate at 60° C., the mixture was heated to 120° C. at 1.6 bar abs. for 12 hours. After cooling, the reaction mixture was filtered at 60° C. ($m_{Ru}$(FK)=0.024 g) and washed with 20 g of vinyl acetate, whereupon 83.0 g of a red-brown filtrate were obtained with a Ru content of 0.24% by weight, based on the total mass of the filtrate.

Comparative Example 2

Preparation of a Catalyst Solution with Low Ru Concentration (<0.5% by Weight) and a Vinyl Ester/Acid Ratio of 1:1

Into a 100 ml Berghoff autoclave were introduced 50.0 g (0.25 mol) of lauric acid, 0.26 g (6.5 mmol) of sodium hydroxide, 0.07 g of phenothiazine and the mixture was heated to 120° C. for 1 hour such that resulting water of reaction could escape. Subsequently, 0.60 g (2 mmol) of ruthenium(III) chloride hydrate was added and the mixture heated to 120° C. for a further half an hour such that water could escape. After addition of 21.5 g (0.25 mol) of vinyl acetate at 60° C., the mixture was heated to 120° C. at 1.2 bar abs. for 12 hours. After cooling, the reaction mixture was filtered at 60° C. ($m_{Ru}$(FK)=0.017 g) and washed with 20 g of vinyl acetate, whereupon 81.4 g of a red-brown filtrate were obtained with a Ru content of 0.28% by weight.

Comparative Example 3

Preparation of a Catalyst Solution with High Ru Concentration (>0.5% by Weight) and a Vinyl Ester/Acid Ratio of 2:1

Into a 100 ml Berghoff autoclave were introduced 38.5 g (0.19 mol) of lauric acid, 1.02 g (25.5 mmol) of sodium hydroxide, 0.07 g of phenothiazine and the mixture was heated to 120° C. for 1 hour such that resulting water of reaction could escape. Subsequently, 2.36 g (8.4 mmol) of ruthenium(III) chloride hydrate were added and the mixture was heated to 120° C. for a further half an hour such that water could escape. After addition of 33.0 g (0.38 mol) of vinyl acetate at 60° C., the mixture was heated to 120° C. at 2.1 bar abs. for 12 hours. After cooling, the reaction mixture was filtered at 60° C. ($m_{Ru}$(FK)=0.378 g) and washed with 25 g of vinyl acetate, whereupon 85.5 g of a red-brown filtrate were obtained with a Ru content of 0.53% by weight.

Example 4

Preparation of a Catalyst Solution with High Ru Concentration (>0.5% by Weight) and a Vinyl Ester/Acid Ratio of 1:1

Into a 100 ml Berghoff autoclave were introduced 50.0 g (0.25 mol) of lauric acid, 1.07 g (27 mmol) of sodium hydroxide, 0.07 g of phenothiazine and the mixture was heated to 120° C. for 1 hour such that resulting water of reaction could escape. Subsequently, 2.36 g (8.4 mmol) of ruthenium(III) chloride hydrate were added and the mixture was heated to 120° C. for a further half an hour such that water could escape. After addition of 21.5 g (0.25 mol) of vinyl acetate at 60° C., the mixture was heated to 120° C. at 4.9 bar abs. for 12 hours. After cooling, the reaction mixture was filtered at 60° C. ($m_{Ru}$(FK)=0.013 g) and washed with 25 g of vinyl acetate, whereupon 88.4 g of a red-brown filtrate were obtained with a Ru content of 1.10% by weight.

Example 5

Preparation of a Catalyst Solution with High Ru Concentration (>0.5% by Weight) and a Vinyl Ester/Acid Ratio of 1:1

Into a 100 ml Berghoff autoclave were introduced 50.0 g (0.25 mol) of lauric acid, 1.73 g (43 mmol) of sodium hydroxide, 0.07 g of phenothiazine and the mixture was heated to 120° C. for 1 hour such that resulting water of reaction could escape. Subsequently, 3.80 g (13.5 mmol) of ruthenium(III) chloride hydrate were added and the mixture was heated to 120° C. for a further half an hour such that water could escape. After addition of 21.5 g (0.25 mol) of vinyl acetate at 60° C., the mixture was heated to 120° C. at 4.9 bar abs. for 12 hours. After cooling, the reaction mixture was filtered at 60° C. ($m_{Ru}$(FK)=0.258 g) and washed with 25 g of vinyl acetate, whereupon 65.9 g of a red-brown filtrate were obtained with a Ru content of 1.76% by weight.

|  | Ru concentration [wt %] | | Ru yield [%] |
| --- | --- | --- | --- |
|  | Start* | After washing |  |
| Comparative example 1 | 0.3 | 0.24 | 89 |
| Comparative example 2 | 0.3 | 0.28 | 93 |
| Comparative example 3 | 1.2 | 0.53 | 55 |
| Example 4 | 1.2 | 1.10 | 99 |
| Example 5 | 1.9 | 1.76 | 82 |

*based on the sum total of lauric acid and vinyl acetate

Comparative example 1 and comparative example 2 show that, at Ru concentrations of less than 0.5% by weight, the lowering of the vinyl acetate/lauric acid ratio leads to an increased Ru yield. This effect is revealed more radically on increasing the Ru concentration. A Ru yield of only 55% by weight is obtained in comparative example 3 compared to example 4.

Example 6

Use of the Active Ru Catalyst Solution with a Ru Content >0.5% by Weight in the Transvinylation of Lauric Acid with Vinyl Acetate In a 100 ml Berghoff autoclave, 25.0 g of lauric acid, 43.0 g of vinyl acetate and 2.81 g of Ru catalyst solution from example 4 (1.10% by weight ruthenium) were heated at 140° C. at 3 bar abs. for 3 hours. After cooling, the reaction mixture was analyzed by quantitative NMR spectroscopy. A yield of vinyl laurate of 78% was achieved in this case.

The example shows that the Ru catalyst solution according to the invention can be used in the transvinylation of carboxylic acids.

The invention claimed is:
1. A method for the preparation of an active ruthenium catalyst solution, which is effective to catalyze transvinylation of a reactant vinyl ester with a reactant carboxylic acid to generate a product vinyl ester without an additional formation step, said method comprising: carrying out a reaction of at least one ruthenium(III) halide with at least one inorganic or organic base, at least one reactant vinyl ester and at least one reactant carboxylic acid to provide the active ruthenium catalyst solution, wherein:

a) the reaction is conducted at a temperature of 70° C. to 170° C.,
b) a molar ratio of the at least one reactant vinyl ester to the at least one reactant carboxylic acid is from 1:1.8 to 1.8:1,
c) the at least one ruthenium(III) halide is used in an amount of ≥0.5% by weight of Ru metal based on a total weight of the at least one reactant vinyl ester and the at least one reactant carboxylic acid, and
d) the active ruthenium catalyst solution has a ruthenium concentration greater than 0.5% by weight of Ru metal, based on a total weight of the active ruthenium catalyst solution.

2. The method as claimed in claim 1, wherein the at least one ruthenium(III) halide is used in an amount of 0.75% by weight to 3% by weight of Ru metal, based on the total weight of the at least one reactant vinyl ester and the at least one reactant carboxylic acid.

3. The method as claimed in claim 1, wherein a carboxylic vinyl ester of the general formula R—C(O)O—CH=CH$_2$ is used as the at least one reactant vinyl ester, where R is an aliphatic residue having 1 to 12 carbon atoms, a cycloaliphatic residue having up to 12 carbon atoms, or an aromatic residue having up to 12 carbon atoms.

4. The method as claimed in claim 1, wherein a carboxylic acid of the general formula R'—COOH is used as the at least one reactant carboxylic acid, where R' is an aliphatic residue having 1 to 22 carbon atoms, a cycloaliphatic residue having up to 22 carbon atoms, or an aromatic residue having up to 22 carbon atoms.

5. The method as claimed in claim 1, wherein the molar ratio of the at least one reactant vinyl ester to the at least one reactant carboxylic acid is from 1.5:1 to 1:1.

6. The method as claimed in claim 1, wherein the base and the at least one reactant carboxylic acid are pretreated at a temperature of 80° C. to 160° C. and a pressure of ≤1 bar abs., then the at least one Ru(III) halide is added and the reaction is continued under the same pressure and temperature conditions, then reactant vinyl ester is added and the reaction continued at a temperature of 70° C. to 170° C. and a pressure of >1 bar abs.

7. The method as claimed in claim 2, wherein a carboxylic vinyl ester of the general formula R—C(O)O—CH=CH$_2$ is used as the at least one reactant vinyl ester, where R is an aliphatic residue having 1 to 12 carbon atoms, a cycloaliphatic residue having up to 12 carbon atoms, or an aromatic residue having up to 12 carbon atoms.

8. The method as claimed in claim 7, wherein a carboxylic acid of the general formula R'—COOH is used as the at least one reactant carboxylic acid, where R' is an aliphatic residue having 1 to 22 carbon atoms, a cycloaliphatic residue having up to 22 carbon atoms, or an aromatic residue having up to 22 carbon atoms.

9. The method as claimed in claim 8, wherein the molar ratio of the at least one reactant vinyl ester to the at least one reactant carboxylic acid is from 1.5:1 to 1:1.

10. The method as claimed in claim 9, wherein the base and the at least one reactant carboxylic acid are pretreated at a temperature of 80° C. to 160° C. and a pressure of ≤1 bar abs., then the at least one Ru(III) halide is added and the reaction is continued under the same pressure and temperature conditions, then reactant vinyl ester is added and the reaction continued at a temperature of 70° C. to 170° C. and a pressure of >1 bar abs.

* * * * *